(12) United States Patent
Kobayashi (10) Patent No.: US 9,084,543 B2
(45) Date of Patent: Jul. 21, 2015

(54) X-RAY DIAGNOSTIC APPARATUS

(71) Applicant: Tadaharu Kobayashi, Otawara (JP)

(72) Inventor: Tadaharu Kobayashi, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/706,516

(22) Filed: Dec. 6, 2012

(65) Prior Publication Data

US 2013/0094626 A1    Apr. 18, 2013

Related U.S. Application Data

(63) Continuation of application No. PCT/JP2012/074164, filed on Sep. 21, 2012.

(30) Foreign Application Priority Data

Oct. 6, 2011   (JP) .................................. 2011-221874

(51) Int. Cl.
*A61B 6/03* (2006.01)
*A61B 6/02* (2006.01)
*A61B 6/00* (2006.01)

(52) U.S. Cl.
CPC ................ *A61B 6/032* (2013.01); *A61B 6/027* (2013.01); *A61B 6/4441* (2013.01); *A61B 6/544* (2013.01); *A61B 6/487* (2013.01); *A61B 6/5205* (2013.01)

(58) Field of Classification Search
CPC ...................................................... A61B 6/4441
USPC .............. 378/19, 41, 62, 87, 15, 21, 4, 42, 44
See application file for complete search history.

(56) References Cited

U.S. PATENT DOCUMENTS 6,233,308 B1 * 5/2001 Hsieh ............................... 378/62
7,315,606 B2 * 1/2008 Tsujii .............................. 378/20

(Continued)

FOREIGN PATENT DOCUMENTS

CN          1690845 A    11/2005
CN       101292877 A    10/2008

(Continued)

OTHER PUBLICATIONS

International Search Report and Written Opinion issued Dec. 11, 2012 in PCT /JP2012/074164 (with English translation of Category of Cited Documents).

(Continued)

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

According to one embodiment, an X-ray diagnostic apparatus includes an X-ray source, an X-ray detector, a rotating mechanism, a control unit, and a reconstruction unit. The source irradiates an object with X-rays. The detector outputs projection data by detecting X-rays transmitted through the object. The rotating mechanism rotates the source and the detector around the object. The control unit acquires projection data, while making the rotating mechanism rotate the source and the detector, such that the number of views in a specific view angle range becomes larger than that in other view angle ranges. The reconstruction unit configured to reconstruct an image by using acquired projection data of each view.

8 Claims, 7 Drawing Sheets

(56) References Cited

U.S. PATENT DOCUMENTS

| | | | |
|---|---|---|---|
| 7,684,537 B2* | 3/2010 | Imai et al. ............... | 378/8 |
| 8,094,774 B2* | 1/2012 | Noshi et al. ............. | 378/15 |
| 8,358,824 B2* | 1/2013 | Hagiwara ................ | 382/131 |
| 2004/0254456 A1* | 12/2004 | Ritter ..................... | 600/425 |
| 2006/0256920 A1 | 11/2006 | Tsujii | |
| 2008/0108895 A1* | 5/2008 | Sabol et al. ............. | 600/425 |
| 2009/0022271 A1 | 1/2009 | Ohishi et al. | |
| 2011/0075907 A1* | 3/2011 | Nakanishi .............. | 382/131 |

FOREIGN PATENT DOCUMENTS

| JP | 62-221338 | 9/1987 |
|---|---|---|
| JP | 11-113892 | 4/1999 |
| JP | 2000-271112 | 10/2000 |
| JP | 2003-299644 | 10/2003 |
| JP | 2005-230536 | 9/2005 |
| JP | 2009-22464 | 2/2009 |

OTHER PUBLICATIONS

International Preliminary Report on Patentability and Written Opinion issued Apr. 17, 2014 in PCT/JP2012/074164 (English Translation only).

International Search Report issued Dec. 11, 2012, in International Application No. PCT/JP2012/074164 (submitting English translation only, International Search Report previously filed).

Office Action issued on Sep. 12, 2014 in the corresponding Chinese patent Application No. 201280002376.5 (with English Translation).

* cited by examiner

X-RAY DIAGNOSTIC APPARATUS

CROSS-REFERENCE TO RELATED APPLICATIONS

This application is a Continuation application of PCT Application No. PCT/JP2012/074164, filed Sep. 21, 2012 and based upon and claiming the benefit of priority from Japanese Patent Application No. 2011-221874, filed Oct. 6, 2011, the entire contents of all of which are incorporated herein by reference.

FIELD

Embodiments described herein relate generally to an X-ray diagnostic apparatus having a so-called LCI (Low Contrast Imaging) function of reconstructing a tomographic image of an object.

BACKGROUND

An X-ray diagnostic apparatus is an apparatus which irradiates an object with X-rays from an X-ray source, captures the X-rays transmitted through the patient by using an X-ray detector, and generates an X-ray fluoroscopic image as a shade image proportional to the transit dose. An operator such as a doctor or an examination technician diagnoses an object by observing the X-ray fluoroscopic image generated by the X-ray diagnostic apparatus.

Recently, there has been developed a technique (to be also referred to as LCI) of acquiring the projection data of an object from many directions while rotating the X-ray source and the X-ray detector around the object and obtaining a tomographic image of the object by reconstructing the acquired projection data in the same manner as an X-ray computed tomography apparatus. LCI is used for the visualization and the like of an object exhibiting a relatively small density difference among CT values, such as an organ.

In general, LCI is designed to acquire projection data at a predetermined rate on the orbit of an X-ray source and X-ray detector while keeping X-ray irradiation conditions and the rotational speed of the X-ray source and X-ray detector constant.

Since a sectional shape of a human body is generally elliptic, the body thickness changes depending on the projection direction. Therefore, the body thickness increases in the longitudinal direction of the human body, and the dose of incident X-rays on the X-ray detector becomes lower than that in the widthwise direction. Likewise, even at a region, for example, a shoulder region, in which bones extend together in a specific direction, when the projection direction coincides with the above specific direction, the dose of incident X-rays on the X-ray detector decreases. When the dose of incident X-rays on the X-ray detector becomes lower than a predetermined level, circuit noise in the X-ray detector or X-ray photon quantization noise becomes conspicuous, resulting in a decrease in S/N ratio. As a consequence, streak artifacts appear in the reconstructed image in LCI.

In order to obtain a favorable tomographic image of an object by the LCI function, it is necessary to prevent the occurrence of or reduce artifacts like those described above due to the body thickness change of an object and the like.

DETAILED DESCRIPTION

In general, according to one embodiment, an X-ray diagnostic apparatus includes an X-ray source, an X-ray detector, a rotating mechanism, a control unit, and a reconstruction unit.

The X-ray source irradiates an object with X-rays. The X-ray detector outputs projection data by detecting X-rays transmitted through the object. The rotating mechanism rotates the X-ray source and the X-ray detector around the object while making the X-ray source and the X-ray detector face each other. The control unit acquires projection data, while making the rotating mechanism rotate the X-ray source and the X-ray detector around the object, such that the number of views in a specific view angle range becomes larger than that in other view angle ranges. The reconstruction unit configured to reconstruct an image by using acquired projection data of each view.

The first to third embodiments will be described with reference to the accompanying drawings.

Note that the same reference numerals in the following description denote the same constituent elements, and a repetitive description will be made only when required.

An arrangement common to each embodiment will be described first.

[Overall Arrangement of X-Ray Diagnostic Apparatus]

Figure 1:
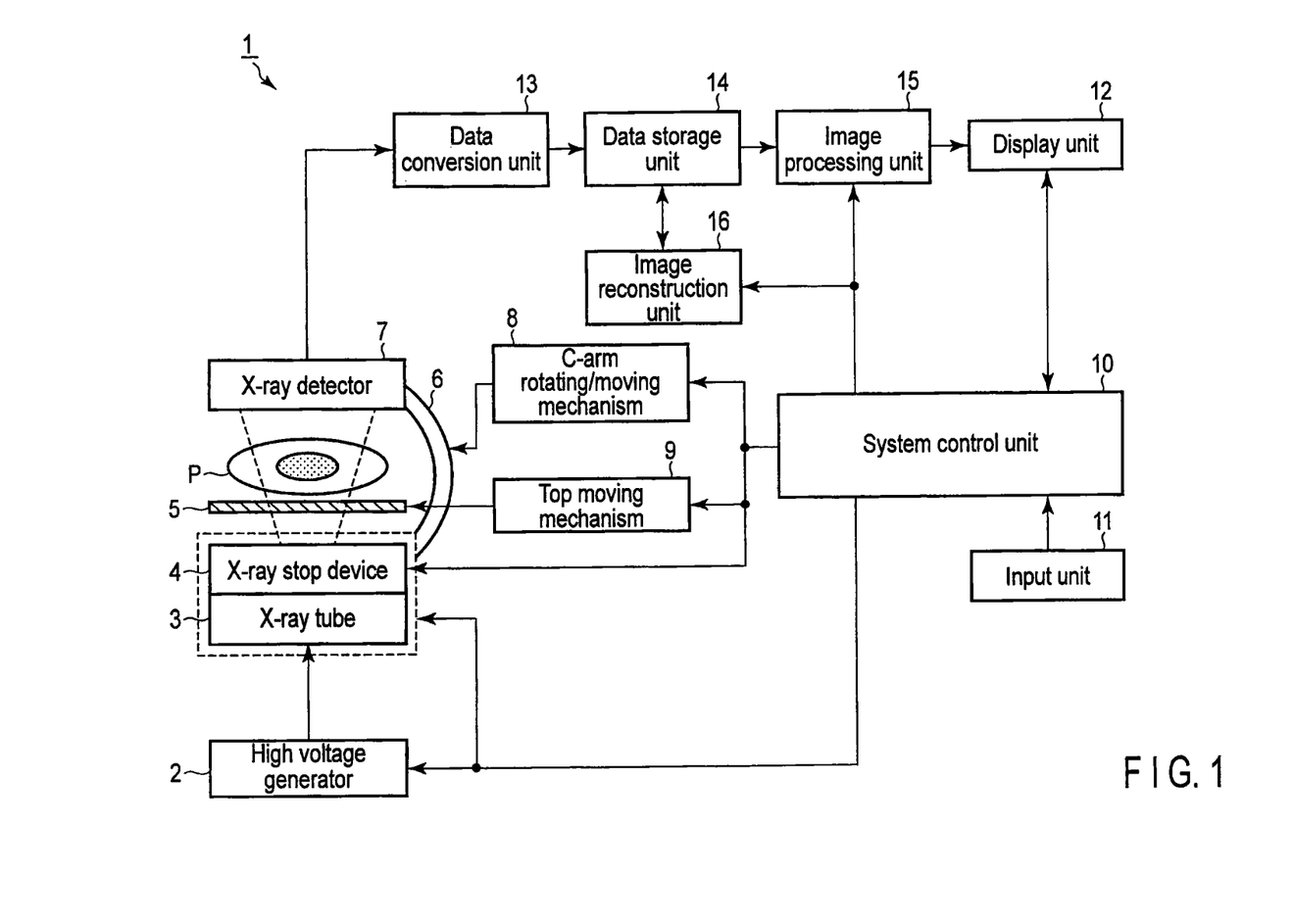
FIG. 1 is a block diagram of an X-ray diagnostic apparatus common to each embodiment.

FIG. 1 is a block diagram of an X-ray diagnostic apparatus 1 common to each embodiment.

As shown in FIG. 1, the X-ray diagnostic apparatus 1 includes a high voltage generator 2, an X-ray tube 3 as an X-ray source, an X-ray stop device 4, a top 5, a C-arm 6, an X-ray detector 7, a C-arm rotating/moving mechanism 8, a top moving mechanism 9, a system control unit 10 (controller), an input unit 11, a display unit 12, a data conversion unit 13, a data storage unit 14, an image processing unit 15, and an image reconstruction unit 16.

The high voltage generator 2 generates a high voltage to be applied to the X-ray tube 3. The X-ray tube 3 generates X-rays based on the high voltage applied from the high voltage generator 2.

The X-ray stop device 4 is a device for focusing X-rays generated from the X-ray tube 3 so as to selectively irradiate a region of interest in an object P with X-rays. For example, the X-ray stop device 4 has four slidable aperture vanes. Sliding these aperture vanes will focus X-rays.

The top 5 is a bed on which the object P is placed, and is arranged on the bedstead (not shown).

The X-ray detector 7 includes a plurality of X-ray detection elements which detect the X-rays transmitted through the object P. Each of these X-ray detection elements converts the X-rays emitted from the X-ray tube 3 and transmitted through the object P into electrical signals and accumulates them.

The C-arm 6 holds the X-ray tube 3, the X-ray stop device 4, and the X-ray detector 7 while making them face each other through the object P.

The C-arm rotating/moving mechanism 8 is a device for rotating and moving the C-arm 6. The top moving mechanism 9 is a device for moving the top 5.

The data conversion unit 13 reads the charges accumulated in the X-ray detector 7 in synchronism with X-ray pulse irradiation. The data conversion unit 13 also converts a read electrical signal into digital data, and outputs it to the data storage unit 14. The data storage unit 14 stores the digital data output from the data conversion unit 13 as projection data.

The image processing unit 15 performs various types of image processing such as window transformation and RGB processing for the projection data stored in the data storage unit 14, and outputs the resultant image as each X-ray fluoroscopic image to the display unit 12.

The input unit 11 includes a mouse, keyboard, buttons, trackball, and joy stick which are used by the operator who operates the X-ray diagnostic apparatus 1, such as a doctor or a technician, to input various types of commands and information, and outputs the commands and information input with these devices to the system control unit 10.

The display unit 12 includes a monitor such as an LCD (Liquid Crystal Display) or a CRT (Cathode Ray Tube), and displays a GUI (Graphical User Interface) for accepting an input from the operator via the input unit 11 or the X-ray fluoroscopic image input from the image processing unit 15.

The system control unit 10 controls the overall operation of the X-ray diagnostic apparatus 1. That is, the system control unit 10 performs adjustment of the dose of X-rays to be applied to the object P, ON/OFF control for X-ray irradiation, rotation/movement control on the C-arm 6, movement control on the top 5, and the like by controlling the high voltage generator 2, the C-arm rotating/moving mechanism 8, the X-ray stop device 4, and the like based on commands and the like input by the operator via the input unit 11.

The system control unit 10 controls the image processing unit 15 and the image reconstruction unit 16 based on commands and the like input by the operator via the input unit 11. The system control unit 10 controls the display unit 12 to display the above GUI.

Figure 2:
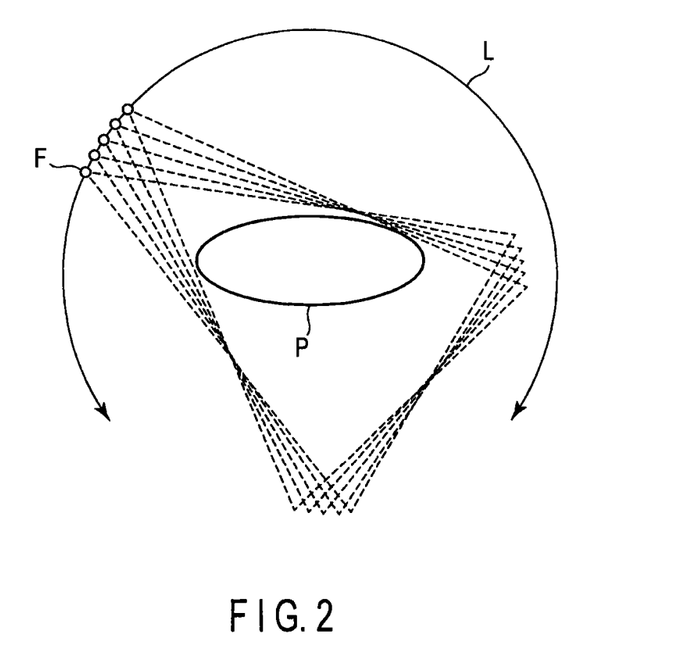
FIG. 2 is a view for explaining projection data (view data) acquisition by the X-ray diagnostic apparatus.

As shown in FIG. 2, the X-ray diagnostic apparatus 1 according to this embodiment has a function (to be referred to an LCI function hereinafter) of acquiring projection data (view data) of the object from many directions while rotating an X-ray focus F around the object P and obtaining a tomographic image of the object by reconstructing the acquired view data like an X-ray computed tomography apparatus. Referring to FIG. 2, reference symbol L denotes the locus of the X-ray focus F, and the broken lines indicate X-ray irradiation ranges at the respective X-ray focuses F. In general, the X-ray focus F is rotated within the range of about 0° to 240° to obtain several hundred view data during the rotation. For the sake of descriptive convenience, referring to FIG. 2, each X-ray focus F is plotted while the distances between focuses are increased (as in FIGS. 5, 8, and 11).

The system control unit 10 controls the high voltage generator 2 to cause the X-ray tube 3 to perform X-ray pulse irradiation at an arbitrary period. Making the data conversion unit 13 read charges from the X-ray detector 7 in synchronism with X-ray pulse irradiation can acquire view data at the period. The period of this view data acquisition will be referred to as a frame rate hereinafter.

The data storage unit 14 stores many view data output from the data conversion unit 13 at the time of the operation of the LCI function, together with view angle information representing view angles at the time of imaging. In this case, a view angle is the gradient of a straight line connecting the X-ray tube 3 and the X-ray detector 7 relative to a straight line connecting the X-ray tube 3 and the X-ray detector 7 at default positions. The image reconstruction unit 16 reconstructs a tomographic image of the object P by performing so-called back projection processing of superimposing the respective view data stored in the data storage unit 14 along the projection beams based on view angle information. The data storage unit 14 stores the reconstructed image obtained by reconstruction using the image reconstruction unit 16. The image processing unit 15 performs various types of image processing such as window transformation and RGB processing for the reconstructed image stored in the data storage unit 14, and outputs the resultant image to the display unit 12. The display unit 12 displays the reconstructed image input from the image processing unit 15.

Figure 3:
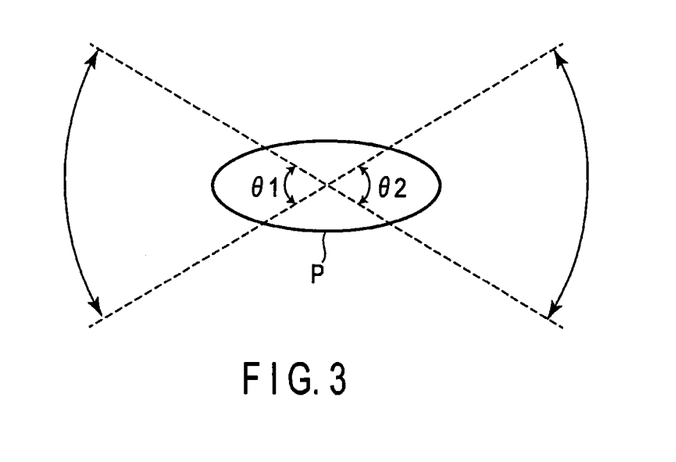
FIG. 3 is a view showing specific view angle ranges in which the S/N ratio decreases at the time of the acquisition of projection data.

Assuming that the object P is a human body, since the body thickness is not constant, the S/N ratios of outputs from the X-ray detector 7 decrease in specific view angle ranges θ1 and θ2, as shown in FIG. 3. As a consequence, streak artifacts appear in reconstructed images.

A technique of preventing the occurrence of or reducing artifacts will be described in the first to third embodiments.

First Embodiment

This embodiment is configured to increase the number of views to be acquired in the specific view angle ranges θ1 and θ2 by increasing a frame rate R in the view angle ranges θ1 and θ2 while rotating an X-ray tube 3 and an X-ray detector 7 at a constant speed ωd. The embodiment is configured to prevent the occurrence of or reduce the streak artifacts by reconstructing an image by using acquired view data.

Concrete operation of the X-ray diagnostic apparatus 1 according to this embodiment will be described with reference to FIGS. 4, 5, and 6.

Figure 4:
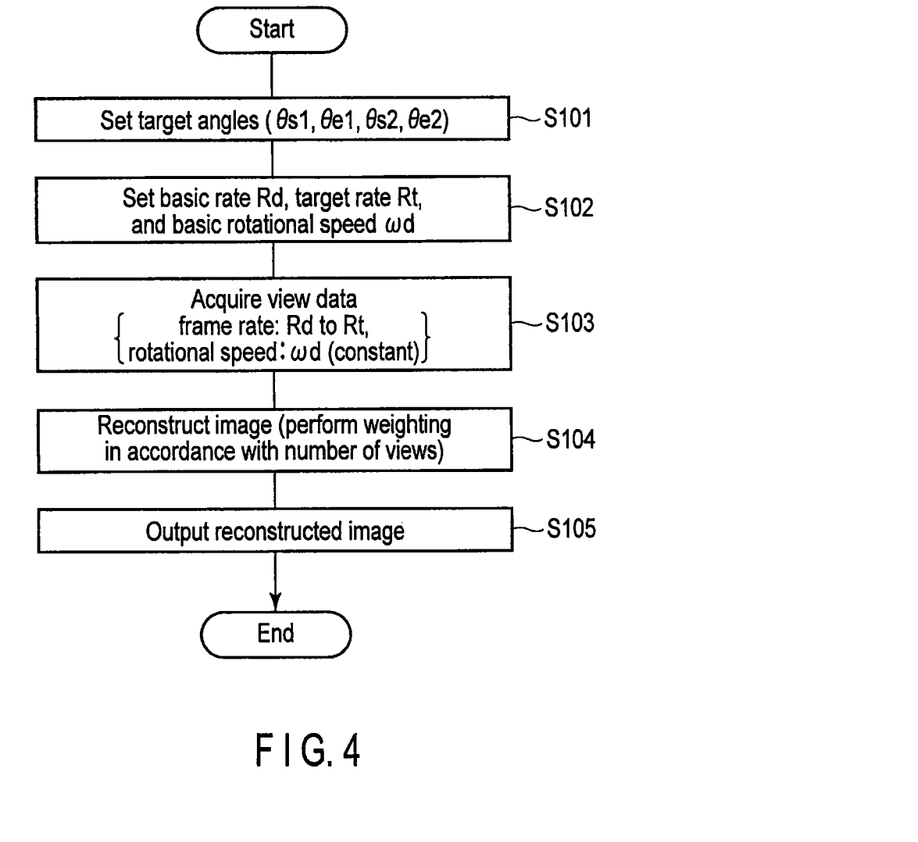
FIG. 4 is a flowchart showing the operation of an X-ray diagnostic apparatus according to the first embodiment.

In response to a user's instruction to generate an image by using the LCI function, the apparatus starts the processing shown in the flowchart of FIG. 4. First of all, a system control unit 10 sets view angle ranges in which the number of views should be increased (step S101).

Figure 5:
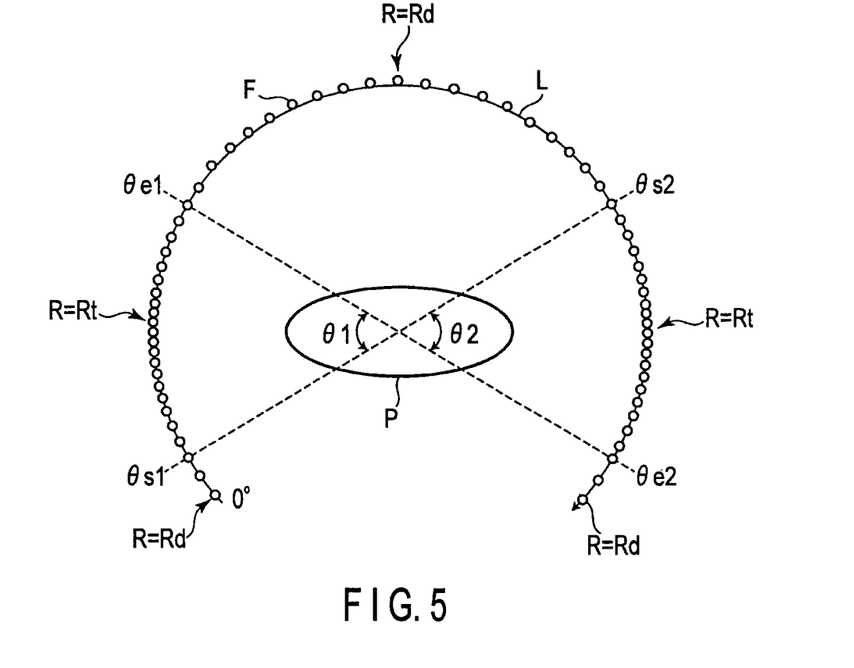
FIG. 5 is a view for explaining projection data acquisition according to this embodiment.

More specifically, as shown in FIG. 5, assuming that the start point of rotation of a C-arm 6 is a reference point (0°), the system control unit 10 sets a rotational angle θs1 from the reference point to the start point of a view angle range θ1, a rotational angle θe1 to the end point of the view angle range θ1, a rotational angle θs2 to the start point of a view angle range θ2, and a rotational angle θe2 from the end point of the view angle range θ2. The system control unit 10 may set the values of the rotational angles θs1, θe1, θs2, and θe2 to the values input by an operator such as a doctor or a technician via the input unit 11 or may automatically be set to preset fixed values.

The system control unit 10 then sets a rate Rd which is the basic frame rate of view data acquisition, a rate Rt (Rd≤Rt) which is a target frame rate in the view angle ranges θ1 and θ2, and the rotational speed ωd as the basic rotational speed of the C-arm (step S102). The system control unit 10 may set the values the rate Rd, rate Rt, and rotational speed ωd to the values input by an operator such as a doctor or a technician via the input unit 11 or may be automatically set to preset fixed values.

Note that the system control unit 10 sets parameters necessary for X-ray imaging, other than the rotational angles θs1, θe1, θs2, and θe2 set in steps S101 and S102, the rates Rd and Rt, and the rotational speed ωd, such as a tube voltage to be applied to the X-ray tube 3 and a region of interest by using the information input from the input unit 11, preset fixed values, or the like.

Upon completion of the respective parameters, the system control unit 10 acquires view data in accordance with these parameters (step S103). The data storage unit 14 stores acquired view data.

The acquisition of view data in this embodiment will be described with reference to FIGS. 5 and 6.

FIG. 5 plots the position of an X-ray focus F on a locus L at the time of view data acquisition. The frame rate R increases as the plot intervals decreases, and the vice versa. FIG. 6 shows how the frame rate R changes, with the abscissa representing a rotation amount θ from the reference point (0°) of the C-arm 6, and the ordinate representing a ratio K obtained by dividing the frame rate R by the rate Rd.

In step S103, the system control unit 10 controls the C-arm rotating/moving mechanism 8 to rotate the C-arm 6 at the constant speed ωd. In addition, the system control unit 10 sets the frame rate R to Rd at the beginning of the start of rotation of the C-arm 6, smoothly increases the frame rate R to Rt at around the time when the rotational angle θ of the C-arm 6 reaches θs1, and smoothly decreases the frame rate R to Rd at round the time when the rotational angle θ reaches θe1. Thereafter, the system control unit 10 smoothly increases the frame rate R to Rt at around the time when the rotational angle θ of the C-arm 6 reaches θs2, and smoothly decreases the frame rate R to Rd at around the time when the rotational angle θ reaches θe2.

Subsequently, when the rotational angle θ of the C-arm 6 reaches the end point, the system control unit 10 causes a C-arm rotating/moving mechanism 8 to stop rotating the C-arm 6, causes the high voltage generator 2 to stop applying a voltage to the X-ray tube 3, and terminates the acquisition of view data.

With the above control, the number of views in the view angle ranges θ1 and θ2 becomes larger than that in other view angle ranges.

After step S103, an image reconstruction unit 16 reconstructs an image by using acquired view data stored in a data storage unit 14 (step S104). Note that the image reconstruction unit 16 performs back projection processing upon correcting the view data of the view angle ranges in which the number of views has been increased, in accordance with the ratio at which the number of views has been increased.

This embodiment performs the above correction by using a coefficient A defined by equation (1).

$$A = 1/K (= Rd/R) \quad (1)$$

where R is a frame rate at the time of acquisition of each view data. In the above correction, the image reconstruction unit 16 calculates the coefficient A for each view data by using equation (1), and weights each view data by multiplying each numerical value included in the corresponding view data by the calculated coefficient A.

Using view data having undergone such correction will maintain the consistency of view data at each view angle, and hence can reconstruct an accurate tomographic image. The data storage unit 14 stores the image reconstructed in step S104.

After step S104, an image processing unit 15 performs various types of image processing for the reconstructed image stored in the data storage unit 14 and outputs the resultant image to a display unit 12 (step S105). The display unit 12 displays the reconstructed image input from the image processing unit 15.

After step S105, the apparatus completes the series of processing shown in the flowchart of FIG. 4.

As described above, the X-ray diagnostic apparatus 1 according to this embodiment increases the number of views to be acquired in the specific view angle ranges θ1 and θ2 by increasing the frame rate R in the view angle ranges θ1 and θ2 while rotating the X-ray tube 3 and the X-ray detector 7 at the constant speed ωd. The apparatus then reconstructs an image by using each acquired view data. With this arrangement, the apparatus obtains view data upon increasing the dose of X-rays to be applied in the view angle ranges θ1 and θ2, that is, the angle ranges in which the body thickness of the object P is large. This make it possible to improve the S/N ratio from the viewpoint of all the view data in the view angle ranges θ1 and θ2 and prevent the occurrence of or reduce streak artifacts in a reconstructed image.

The X-ray diagnostic apparatus 1 according to this embodiment reconstructs an image upon correcting the respective view data belonging to the view angle ranges θ1 and θ2 in accordance with the ratio at which the number of views has increased. This can maintain the consistency of view data at the respective view angles and obtain an accurate reconstructed image.

Note that an X-ray CT apparatus includes a correction system which provides, between the X-ray tube and an object, a reference detector for detecting the X-rays emitted from the X-ray tube, and increases the dose of X-rays emitted from the X-ray tube in a specific view angle range by adjusting a tube current while referring to the detection result obtained by the reference detector, thereby improving the S/N ratio. It is, however, difficult to introduce such correction system for an X-ray diagnostic apparatus because the apparatus is not suitable to be provided with a reference detector in consideration of a necessary space and the like. In contrast to this, the arrangement of this embodiment allows to introduce a correction system because it is possible to improve the S/N ratio in a specific view angle range without providing any special constituent element such as a reference detector.

The arrangement of this embodiment can obtain other various advantageous effects.

Second Embodiment

The second embodiment will be described next.

This embodiment differs from the first embodiment in that it increases the number of views in specific view angle ranges θ1 and θ2 by changing a rotational speed ω of a C-arm 6 instead of changing a frame rate R at the time of view data acquisition.

Concrete operation of an X-ray diagnostic apparatus 1 according to this embodiment will be described with reference to FIGS. 7, 8, and 9.

Figure 7:
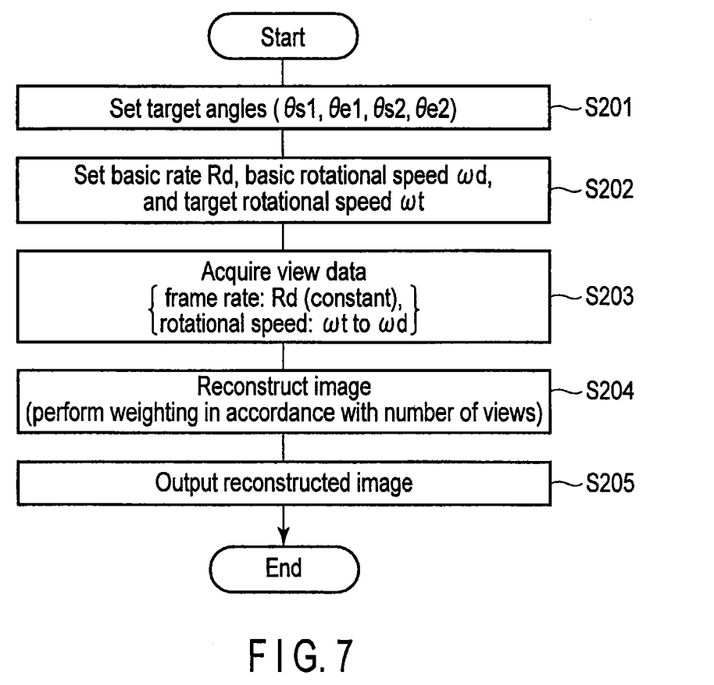
FIG. 7 is a flowchart showing the operation of an X-ray diagnostic apparatus according to the second embodiment.

When the user issues an instruction to generate an image by using the LCI function, the apparatus starts the processing shown in the flowchart of FIG. 7. First of all, a system control unit 10 sets view angle ranges (rotational angles θs1, θe1, θs2, and θe2) in which the number of views is to be increased, as in step S101 (step S201).

The system control unit 10 sets a rate Rd which is the basic frame rate of view data acquisition, a rotational speed ωd as the basic rotational speed of the C-arm, and a rotational speed ωt (ωd≥ωt) as a target rotational speed in the view angle ranges θ1 and θ2 (step S202). The system control unit 10 may set the values the rate Rd, rotational speed ωd, and rotational speed ωt to the values input by an operator such as a doctor or a technician via an input unit 11 or may be automatically set to preset fixed values.

Note that the system control unit 10 sets parameters necessary for X-ray imaging, other than the rotational angles θs1, θe1, θs2, and θe2, the rate Rd, and the rotational speeds ωd and ωt set in steps S201 and S202, by using the information input from the input unit 11, preset fixed values, or the like.

Upon completion of setting of the respective parameters, the system control unit 10 acquires view data in accordance with these parameters (step S203). A data storage unit 14 stores the acquired view data.

The acquisition of view data in this embodiment will be described with reference to FIGS. 8 and 9.

Figure 8:
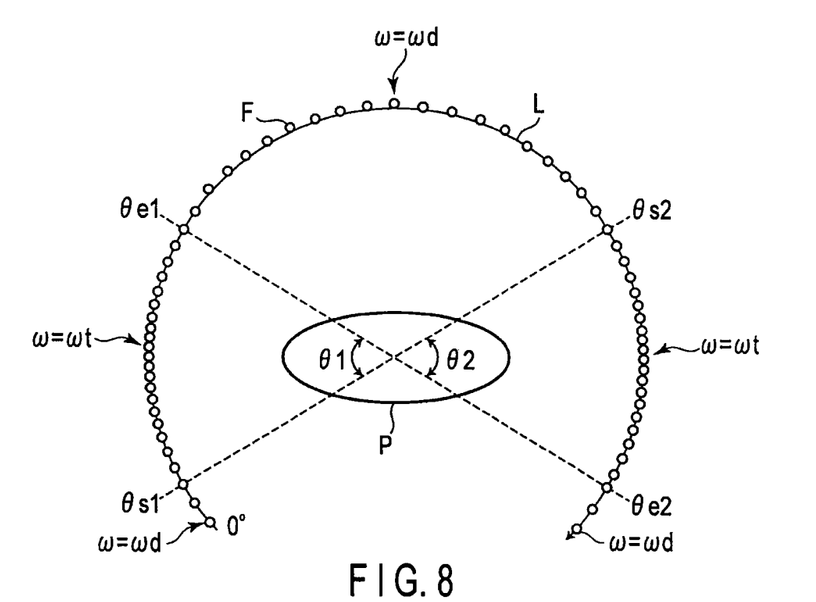
FIG. 8 is a view for explaining projection data acquisition according to this embodiment.

Like FIG. 5, FIG. 8 plots the position of an X-ray focus F on a locus L at the time of view data acquisition. FIG. 9 shows how the rotational speed ω changes, with the abscissa representing a rotation amount θ from the reference point (0°) of the C-arm 6, and the ordinate representing a ratio K obtained by dividing the rotational speed ω by the rotational speed ωd.

In step S203, the system control unit 10 keeps the frame rate R constant at the rate Rd and acquires view data. The system control unit 10 also controls a C-arm rotating/moving mechanism 8 to set the rotational speed ω to ωd at the beginning of the start of view data acquisition, smoothly decreases the rotational speed ω to ωt at around the time when the rotational angle θ of the C-arm 6 reaches θs1, and smoothly increases the rotational speed ω to ωd at around the time when the rotational angle θ reaches θe1. Thereafter, the system control unit 10 smoothly decreases the rotational speed ω to ωt at around the time when the rotational angle θ of the C-arm 6 reaches θs2, and smoothly increases the rotational speed ω to ωd at around the time when the rotational angle θ reaches θe2. Subsequently, when the rotational angle θ of the C-arm 6 reaches the end point, the system control unit 10 causes the C-arm rotating/moving mechanism 8 to stop rotating the C-arm 6, causes a high voltage generator 2 to stop applying a voltage to an X-ray tube 3, and terminates the acquisition of view data.

With the above control, as in the first embodiment, the number of views in the view angle ranges θ1 and θ2 becomes larger than that in other view angle ranges.

After step S203, an image reconstruction unit 16 reconstructs an image by using acquired view data stored in the data storage unit 14 (step S204).

Note that as in the first embodiment, the image reconstruction unit 16 performs back projection processing upon correcting the view data of the view angle ranges in which the number of views has been increased, in accordance with the ratio at which the number of views has been increased.

This embodiment performs the above correction by using a coefficient A defined by equation (2).

$$A = K(=\omega/\omega d) \quad (2)$$

where ω is the rotational speed of the C-arm 6 at the time of acquisition of each view data. In the above correction, the image reconstruction unit 16 calculates the coefficient A for each view data by using equation (2), and weights each view data by multiplying each numerical value included in the corresponding view data by the calculated coefficient A. The data storage unit 14 stores the image reconstructed by using each view data having undergone correction.

After step S204, an image processing unit 15 performs various types of image processing for the reconstructed image stored in the data storage unit 14 and outputs the resultant image to a display unit 12 (step S205). The display unit 12 displays the reconstructed image input from the image processing unit 15.

After step S205, the apparatus completes the series of processing shown in the flowchart of FIG. 7.

As described above, the X-ray diagnostic apparatus 1 according to this embodiment increases the number of views in the specific view angle ranges θ1 and θ2 by decreasing the rotational speed ω of the C-arm 6 in the view angle ranges θ1 and θ2 while causing the X-ray tube 3 and an X-ray detector 7 to acquire view data at the constant frame rate Rd. The apparatus then reconstructs an image by using each acquired view data. As in the first embodiment, with this arrangement, view data are obtained after the dose of X-rays to be applied in the angle ranges in which the body thickness of the object P is large. This make it possible to improve the S/N ratio from the viewpoint of all the view data in the view angle ranges θ1 and θ2 and prevent the occurrence of or reduce streak artifacts in a reconstructed image.

The arrangement of this embodiment can obtain other various advantageous effects in addition to those described in the first embodiment.

Third Embodiment

The third embodiment will be described next.

This embodiment differs from the first and second embodiments in that it acquires view data from the entire surrounding of an object P by rotating a C-arm 6 in a given direction, and then increases the number of views in specific view angle ranges θ1 and θ2 by acquiring view data in the view angle ranges θ1 and θ2 again by rotating the C-arm 6 in the reverse direction.

Concrete operation of an X-ray diagnostic apparatus 1 according to this embodiment will be described with reference to FIGS. 10 and 11.

Figure 10:
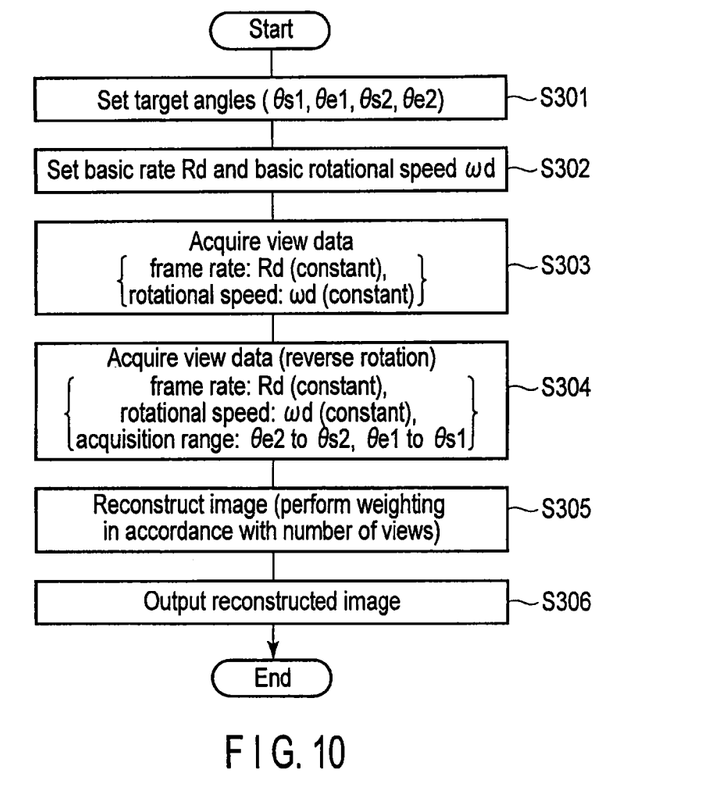
FIG. 10 is a flowchart showing the operation of an X-ray diagnostic apparatus according to the third embodiment.

When the user issues an instruction to generate an image by using the LCI function, the apparatus starts the processing shown in the flowchart of FIG. 10. First of all, a system control unit 10 sets view angle ranges (rotational angles θs1, θe1, θs2, and θe2) in which the number of views is to be increased, as in step S101 (step S301).

The system control unit 10 sets a rate Rd which is the basic frame rate of view data acquisition and a rotational speed ωd as the basic rotational speed of the C-arm (step S302). The system control unit 10 may set the values the rate Rd and rotational speed ωd to the values input by an operator such as a doctor or a technician via an input unit 11 or may be automatically set to preset fixed values.

Note that the system control unit 10 sets parameters necessary for X-ray imaging, other than the rotational speeds θs1, θe1, θs2, and θe2, the rate Rd, and the rotational speed ωd set in steps S301 and S302, by using the information input from the input unit 11, preset fixed values, or the like.

Upon completion of setting of the respective parameters, the system control unit 10 acquires view data in accordance with these parameters. Note however that in this embodiment, the system control unit 10 acquires view data while rotating the C-arm 6 in a given direction (step S303). Thereafter, the system control unit 10 acquires view data again while rotating the C-arm in the reverse direction (step S304). A data storage unit 14 stores the acquired view data.

The acquisition of view data in this embodiment will be described in detail with reference to FIG. 11.

Figure 11:
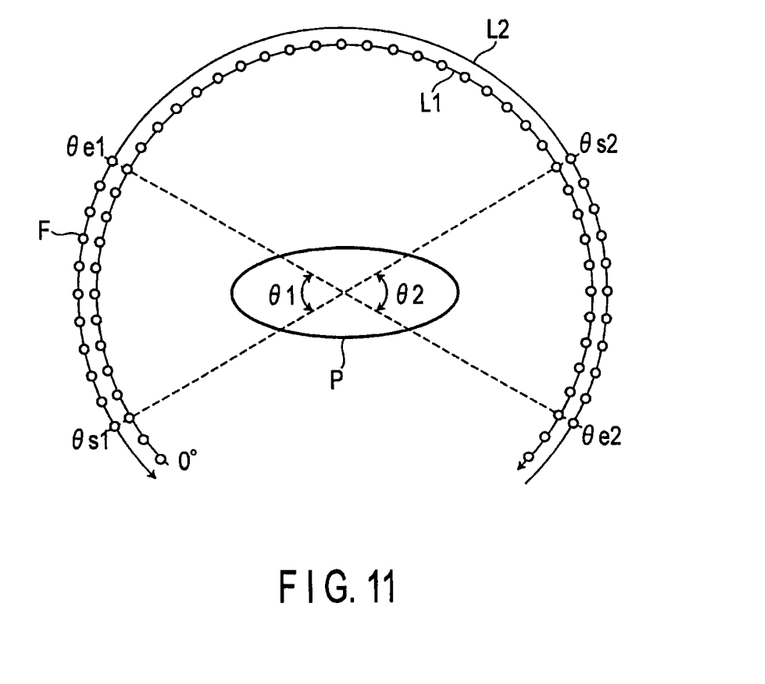
FIG. 11 is a view for explaining projection data acquisition according to this embodiment.

Like FIG. 5, FIG. 11 plots the position of an X-ray focus F on loci L1 and L2 at the time of view data acquisition. Note that the locus L1 is the locus of an X-ray focus which is recorded as the C-arm 6 rotates in step S303, and the locus L2 is the locus of an X-ray focus which is recorded as the C-arm 6 rotates in step S304. For the sake of descriptive convenience, although the loci L1 and L2 are located on the same spatial coordinates, FIG. 11 shows their positions in a slightly shifted state.

In step S303, the system control unit 10 keeps the rotational speed $\omega$ of the C-arm 6 constant at $\omega d$, and the frame rate R constant at Rd, and acquires view data from view angles throughout the entire surrounding of the object P.

In step S304, the system control unit 10 keeps the rotational speed $\omega$ constant at $\omega d$ and reversely rotates the C-arm 6. Note however that the system control unit 10 does not acquire view data until the rotational angle $\theta$ returns to $\theta e2$, keeps the frame rate R constant at Rd when the rotational angle $\theta$ reaches $\theta e2$, and starts view data acquisition. When the rotational angle $\theta$ reaches $\theta s2$, the system control unit 10 stops acquiring view data. Subsequently, when the rotational angle $\theta$ of the C-arm 6 reaches $\theta e1$, the system control unit 10 keeps the frame rate R constant at Rd, and starts view data acquisition again. When the rotational angle $\theta$ reaches $\theta s1$, the system control unit 10 stops acquiring view data.

With the above control, the number of views in the view angle ranges $\theta 1$ and $\theta 2$ becomes larger than that in other view angle ranges as in the first and second embodiments.

After step S304, an image reconstruction unit 16 reconstructs an image by using acquired view data stored in the data storage unit 14 (step S305).

Note that the image reconstruction unit 16 performs back projection processing upon correcting the view data of the view angle ranges in which the number of views has been increased, in accordance with the ratio at which the number of views has been increased, as in the first and second embodiments. This embodiment simply acquires view data in the view angle ranges $\theta 1$ and $\theta 2$ twice as much as that in other view angle ranges. The image reconstruction unit 16 therefore weights each view data by multiplying each numerical value included in the view data belonging to the view angle ranges $\theta 1$ and $\theta 2$ by a coefficient of 0.5, and multiplying each numerical value included in the view data belonging to other view angle ranges by a coefficient of 1.0 (or no coefficient). The data storage unit 14 stores the image reconstructed in step S305.

After step S305, the image processing unit 15 performs various types of image processing for the reconstructed image stored in the data storage unit 14 and outputs the resultant image to a display unit 12 (step S306). The display unit 12 displays the reconstructed image input from the image processing unit 15.

After step S306, the apparatus completes the series of processing shown in the flowchart of FIG. 10.

As described above, the X-ray diagnostic apparatus 1 according to this embodiment acquires view data while rotating an X-ray tube 3 and an X-ray detector 7 around the object P a plurality of times, increases the number of views in the specific view angle ranges $\theta 1$ and $\theta 2$ by omitting the acquisition of projection data in view angle ranges other than the view angle ranges $\theta 1$ and $\theta 2$ at the time of at least one rotation (at the time of reverse rotation in this embodiment), and reconstructs an image by using acquired each view data. This arrangement can also obtain view data upon increasing the dose of X-rays to be applied in the angle ranges in which the body thickness of the object P is large. This makes it possible to improve the S/N ratio from the viewpoint of all the view data in the view angle ranges $\theta 1$ and $\theta 2$ and prevent the occurrence of or reduce streak artifacts in a reconstructed image.

The arrangement of this embodiment can obtain other various advantageous effects in addition to those described in the first and second embodiments.

(Modification)

The arrangements disclosed in the first to third embodiments can be implemented upon proper modification.

For example, the first to third embodiments have exemplified the case in which the number of views to be acquired in the two view angle ranges $\theta 1$ and $\theta 2$ is increased. However, the number of ranges in which the number of views is increased may be one or three or more.

Figure 6:
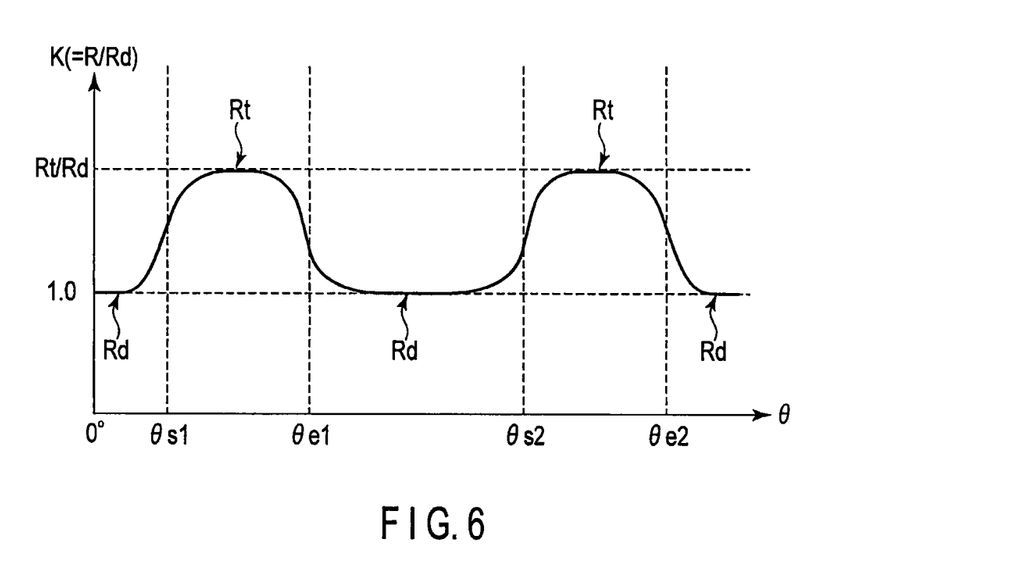
FIG. 6 is a graph showing frame rate changes in projection acquisition according to this embodiment.
Figure 9:
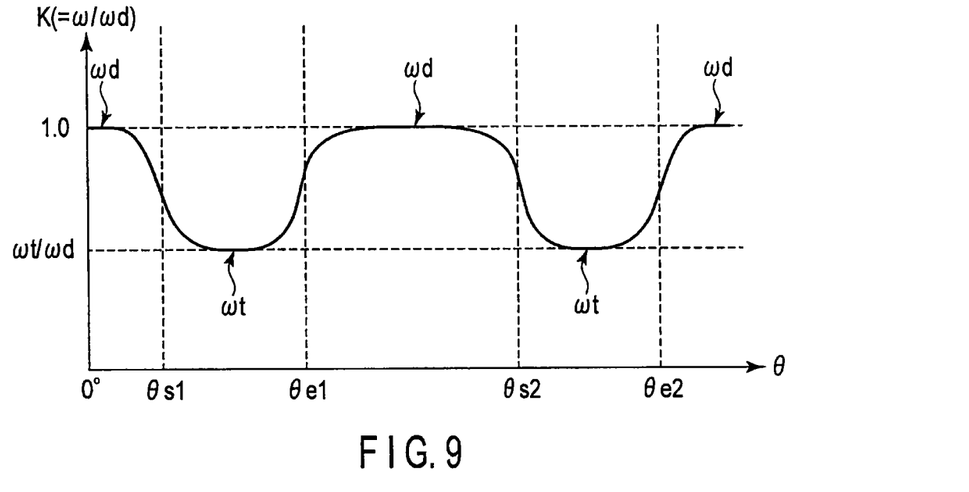
FIG. 9 is a graph showing rotational speed changes in projection data acquisition according to this embodiment.

In addition, the first and second embodiments are configured to smoothly change the frame rate R and the rotational speed $\omega$, as shown in FIGS. 6 and 9. However, the frame rate R and the rotational speed $\omega$ may be changed stepwise with reference to $\theta s1$, $\theta e1$, $\theta s2$, and $\theta e2$ and the like.

The third embodiment has exemplified the case in which view data is acquired during reciprocal rotation of the C-arm 6. However, view data may be acquired while the C-arm 6 is rotated more. Even in this case, it is possible to increase the number of views in the specific view angle ranges $\theta 1$ and $\theta 2$ by omitting the acquisition of projection data in view angle ranges other than the view angle ranges $\theta 1$ and $\theta 2$ at the time of at least one rotation.

Furthermore, it is possible to increase the number of views in the specific view angle ranges $\theta 1$ and $\theta 2$ by properly combining the technique of changing the frame rate R disclosed in the first embodiment, the technique of changing the rotational speed $\omega$ disclosed in the second embodiment, and the technique of acquiring view data throughout many rotations disclosed in the third embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic C-arm shaped angio apparatus comprising:
  an X-ray source configured to irradiate an object with X-rays;
  an X-ray detector configured to output projection data by detecting X-rays transmitted through the object;
  a C-arm shaped rotating mechanism configured to rotate the X-ray source and the X-ray detector around the object while making the X-ray source and the X-ray detector face each other; and
  processing circuitry configured to
    acquire projection data, while making the rotating mechanism rotate the X-ray source and the X-ray detector around the object, such that the number of views in at least one of a first view angle ranges, in which a first body thickness of the object is relatively larger than a second body thickness of the object at other view angle ranges, is greater than the number of views acquired in the other view angle ranges,
    increase the number of views acquired in the at least one of the first view angle ranges by acquiring projection data in both the at least one of the first view angle ranges and the other view angle ranges in a first rotational direction of the C-arm shaped rotating mechanism and acquiring projection data only in the at least one of the first view angle ranges in a second rotational direction of the C-arm shaped rotating mechanism, and reconstruct an image by using acquired projection data of each view.

2. The X-ray diagnostic apparatus of claim 1, wherein the processing circuitry is further configured to increase the number of views in the at least one of the first view angle ranges as compared with the other view angle ranges by increasing a rate of acquisition of the projection data in the at least one of the first view angle ranges while keeping a rotational speed of the C-arm shaped rotating mechanism constant.

3. The X-ray diagnostic apparatus of claim 1, wherein the processing circuitry is further configured to increase the number of views in the at least one of the first view angle ranges as compared with the other view angle ranges by decreasing the rotational speed of the C-arm shaped rotating mechanism in the at least one of the first view angle ranges while keeping a rate of acquisition of the projection data by the X-ray source and the X-ray detector constant.

4. The X-ray diagnostic apparatus of claim 1, wherein the processing circuitry is further configured to increase the number of views in the at least one of the first view angle ranges as compared with the other view angle ranges by acquiring projection data using the X-ray source and the X-ray detector while making the C-arm shaped rotating mechanism rotate the X-ray source and the X-ray detector rotate around the object a plurality of times, and omitting acquisition of projection data in the other view angle ranges at the time of at least one rotation.

5. The X-ray diagnostic apparatus of claim 1, wherein the processing circuitry corrects projection data belonging to a view angle range in which the number of views is increased, in accordance with a ratio at which the number of views is increased, and reconstructs an image using the corrected projection data.

6. The X-ray diagnostic apparatus of claim 1, wherein the at least one of the first view angle ranges is a preset fixed value.

7. The X-ray diagnostic apparatus of claim 1, wherein the first rotational direction of the C-arm shaped rotating mechanism is in a clockwise direction and the second rotational direction of the C-arm shaped rotating mechanism is in a counter-clockwise direction.

8. An X-ray diagnostic method comprising:
irradiating, by an X-ray source, an object with X-rays;
outputting, by an X-ray detector, projection data by detecting X-rays transmitted through the object;
rotating, by a C-arm shaped rotating mechanism, the X-ray source and the X-ray detector around the object while making the X-ray source and the X-ray detector face each other;
acquiring by processing circuitry, projection data, while making the C-arm shaped rotating mechanism rotate the X-ray source and the X-ray detector around the object, such the number of views in the at least one of a first view angle ranges, in which a first body thickness of the object is relatively larger than a second body thickness of the object at other view angle ranges, is greater than the number of views acquired in the other view angle ranges;
increasing by the processing circuitry, the number of views acquired in the at least one of the first view angle ranges by acquiring projection data in both the at least one of the first view angle ranges and the other view angle ranges in a first rotational direction of the C-arm shaped rotating mechanism, and acquiring projection data in only the at least one of the first angle ranges in a second rotational direction of the C-arm shaped rotating mechanism; and
reconstructing an image based on the acquired projection data of each view.

\* \* \* \* \*